quot;US008772294B2

(12) United States Patent
Breu et al.

(10) Patent No.: US 8,772,294 B2
(45) Date of Patent: Jul. 8, 2014

(54) CRYSTALLINE FORMS FOR 5-AMINO-2, 3-DIHYDROPHTHALAZINE-1, 4-DIONE SODIUM SALT, PHARMACEUTICAL PREPARATIONS CONTAINING THE SAME AND METHOD FOR THE PRODUCTION OF SAID FORMS

(75) Inventors: Josef Breu, Bayreuth (DE); Wolfgang Brysch, Berlin (DE); Astrid Kaiser, Berlin (DE); Beate Ludescher, Berlin (DE); Gerrit Maass, Hannover (DE); Thomas Martin, Selb (DE); Wolfgang Milius, Bayreuth (DE); Michael Niedermaier, Berlin (DE)

(73) Assignee: MetrioPharm AG, Zurich (CH)

( * ) Notice: Subject to any disclaimer, the term of this patent is extended or adjusted under 35 U.S.C. 154(b) by 30 days.

(21) Appl. No.: 13/582,522

(22) PCT Filed: Mar. 1, 2011

(86) PCT No.: PCT/EP2011/001124
§ 371 (c)(1),
(2), (4) Date: Sep. 4, 2012

(87) PCT Pub. No.: WO2011/107295
PCT Pub. Date: Sep. 9, 2011

(65) Prior Publication Data
US 2012/0329801 A1 Dec. 27, 2012

(30) Foreign Application Priority Data

Mar. 1, 2010 (EP) .................................. 10002067
Nov. 25, 2010 (EP) .................................. 10075744

(51) Int. Cl.
*A01N 43/58* (2006.01)
*A61K 31/50* (2006.01)
*C07D 237/30* (2006.01)

(52) U.S. Cl.
USPC ......................................... 514/248; 544/237

(58) Field of Classification Search
USPC ......................................... 544/237; 514/248
See application file for complete search history.

(56) References Cited

U.S. PATENT DOCUMENTS

| 5,512,573 | A | 4/1996 | Minin et al. |
| 5,543,410 | A | 8/1996 | Minin et al. |
| 6,489,326 | B1 | 12/2002 | Abidov et al. |
| 7,326,690 | B2 | 2/2008 | Henry et al. |
| 2002/0198208 | A1 | 12/2002 | Abidov et al. |
| 2003/0195183 | A1 | 10/2003 | Zhilov et al. |
| 2008/0194501 | A1 | 8/2008 | Zhilov et al. |
| 2010/0222584 | A1 | 9/2010 | Henry et al. |
| 2011/0275642 | A1 | 11/2011 | Abidov et al. |

FOREIGN PATENT DOCUMENTS

| EP | 0 617 024 | 9/1994 |
| EP | 1 203 587 | 5/2002 |
| RU | 2 113 222 | 6/1998 |
| RU | 2 138 264 | 9/1999 |
| RU | 2 169 139 | 6/2001 |
| RU | 2 211 036 | 8/2003 |
| WO | WO-2010 082858 | 7/2010 |
| WO | WO-2011 107295 | 9/2011 |

OTHER PUBLICATIONS

Abidov, M. T., "Medicinal Preparation," Espacenet, Publication Date: Oct. 27, 2004; English Abstract of RU-2 238 730.
Caira, M. R., "Crystalline Polymorphism of Organic Compounds," Topics in Current Chemistry, 1998, vol. 198, pp. 163-208.
Descotes, J. et al., "Clinical immunotoxicity of therapeutic proteins," Expert Opin. Drug Metab. Toxicol., 2008, vol. 4, No. 12, pp. 1537-1549.
Drew, H. D. K. et al., "Chemiluminescent Organic Compounds. Part II. The Effect of substituents on the Closure of Phthalhydrazides to 5- and 6-Membered Rings," J. Chem. Soc., 1937, vol. 26, pp. 26-33.
EMEA 2008: Guideline on the Specification Limits for Residues of Metal Catalysts or Metal Reagent — EMEA/CHMP/SWP/4446/2000—London, Feb. 21, 2008.
English Translation of RU-2 113 222, Publication Date: Jun. 20, 1998.
English Translation of RU-2 138 264, Publication Date: Sep. 27, 2009.
Griesser, U. J., "The Importance of Solvates," Polymorphisms in the Pharmaceutical Industry, Hilfiker (Ed.), 2006, pp. 211-234.
Haleblian, J. et al., "Pharmaceutical Applications of Polymorphism," Journal of Pharmaceutical Sciences, Aug. 1969, vol. 58, No. 8, pp. 911-929.
Ham, G. et al., "Stability of Trace Iodine Solutions," Analytical Letters, 1979, vol. 12, A5, pp. 535-541.
Hoffmann, J. N., "Immunomodulatory therapies for sepsis: errors of the past?" Intensivmed, 2005, vol. 42, pp. 371-377.
Huntress, E. H. et al., "The preparation of 3-Aminophthallhydrazide for Use in the Demonstration of Chemiluminescence," J. Am Chem. Soc., 1934, vol. 56, pp. 241-242.
International Search Report for PCT/EP2011/001124; Date of actual completion of the international search: Jul. 13, 2011; Date of mailing of the international search report: Jul. 28, 2011.
Metriop Harm AG., "Crystalline forms for 5-amino-2,3-dihydrophthalazine-1,4-dione sodium salt, pharmaceutical preparation containing the same and method for the production of said forms," Espacenet, Publication Date: Sep. 9, 2011 : English Abstract of WO-2011 107295.
Miller, S. P. F. et al., "Scientific Considerations of Pharmaceutical Solid Polymorphism in Regulatory Applications," Polymorphism in the Pharmaceutical Industry, Hilfiker (Ed.), 2006, pp. 385-403.
Ooo Abi, "Medicinal Preparation (variants) and method for its production," Espacenet, Publication Date: Aug. 27, 2003; English Abstract of RU-2 211 036.

(Continued)

*Primary Examiner* — Paul V. Ward
(74) *Attorney, Agent, or Firm* — Millen, White, Zelano & Branigan, P.C.

(57) ABSTRACT

The invention relates to the provision of two novel crystalline forms I and II for 5-amino-2,3-dihydrophthalazine-1,4-dione sodium salt. Surprisingly, it was discovered that form I and form II have differing immunological effects. This advantageous property is useful for immunospecific applications. In addition, both forms have advantageous physicochemical properties, which are useful in the production, further processing and/or use of a pharmaceutical preparation of form I or form II or a mixture of both.

17 Claims, 3 Drawing Sheets

(56) References Cited

OTHER PUBLICATIONS

Predvoditelev, D. A., "Medicinal preparation (variants) and method for its producing," Espacenet, Publication Date: Jul. 27, 2004; English Abstract of RU-2 233 161.

Predvoditelev, D. A., "Method for preparing medicinal preparation," Espacenet, Publication Date: Jan. 27, 2004; English Abstract of RU-2 222 327.

Stott, R. A. W., "Enhanced Chemiluminescence Immunoassay," The Protein Protocols Handbook—2nd Edition, 1998, pp. 1089-1093.

Suntharalingam, G. et al., "Cytokine storm in a Phase 1 Trial of the Anti-CD28 Monoclonal Antibody TGN1412," The New England Journal of Medicine, Sep. 7, 2006, vol. 355, No. 10, pp. 1018-1028.

TS Sovremennoj Meditsiny Medik, "Method for preparing alkali and alkali-earth salts of 5-amino-2,3-dihydro-1,4-phthalazinedione," Espacenet, Publication Date: Jun. 20, 2001; English Abstract of RU-2 169 139.

Williamson, K. L. et al., "Macroscale and Microscale Organic Experiments—2nd Edition," 1994, Chapter 65, pp. 647-654.

English Translation of Diel, R. et al., "Recommendations for tuberculosis-screening initiation of TNF-α-inhibitor treatment in rheumatic disease," Zeitschrift fur Rheumatologie, 2009, vol. 68, pp. 411-416.

English Translation of Bassetti, C. et al., "Escalating immunomodulatory therapy of multiple sclerosis," Sep. 2006.

Translation of an overview printout of "Main Group 51"—Immunomodulators of the "Rote Liste" online database, Feb. 2011.

Translation of a printout of search results concerning available therapeutics for the indication Multiple Sclerosis of the "Rote Liste" online database, Feb. 2011.

English Translation of Ulrich et al., "Crystals with integrated solvents," Nachrichten aus der Chemie, 2005, vol. 53, pp. 19-23.

English Translation of Gundermann, K. D. et al., Configuring and Chemiluminescence, IV, Chemiluminescence in Diazachinones. On the Mechanism of Chemiluminescence in Cyclic Diacylhydrazides, in: Liebigs Annalen der Chemie, vol. 738, pp. 140-160. p. 156: Sodium 3-aminophthalhydrazide (1 page) (1970).

Gundermann, K. D. et al., "Konstitution und, Chemilumineszenz, IV, Chemilumineszenz in Diazachinonen Zum Mechanismus der Chemilumineszenz cyclisher Diacylhydrazide" in: Liebigs Ann. Chem., vol. 738, pp. 140-160. (1970).

CRYSTALLINE FORMS FOR 5-AMINO-2, 3-DIHYDROPHTHALAZINE-1, 4-DIONE SODIUM SALT, PHARMACEUTICAL PREPARATIONS CONTAINING THE SAME AND METHOD FOR THE PRODUCTION OF SAID FORMS

TECHNICAL FIELD OF THE INVENTION

The present invention relates to the provision of at least two novel crystalline forms for 5-amino-2,3-dihydrophthalazine-1,4-dione sodium salt with advantageous properties, pharmaceutical preparations containing the same, and methods for producing the same.

The invention in particular relates to the provision of 2 novel crystalline forms for 5-amino-2,3-dihydrophthalazine-1,4-dione sodium salt with immunostimulating and immunodepressive properties for medical purposes.

BACKGROUND OF THE INVENTION

For quite some time, chemical compounds having immunomodulatory effects are known in the art. To these compounds also belongs 5-amino-2,3-dihydrophthalazine-1,4-dione sodium salt, the compound of the present invention, which is known for instance from the EP 1 203 587 A and has the following basic structure (Na+ not shown):

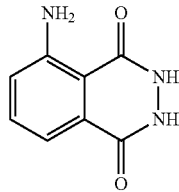 [SMILES: Nc1cccc2c(=O)[nH][nH]c(=O)c12]

The above basic structure is also called luminol. It is known from prior art that 5-amino-2,3-dihydrophthalazine-1,4-dione alkali salts crystallize as solid matter in different hydrate forms. In prior art, in particular the dihydrate of the sodium salt (RU 2113222 C1) and a trihydrate of the potassium salt and mixed forms thereof (RU2211036 C2) are described.

It is known in the art that crystalline forms of a substance can differ in their physical properties such as solubility, dissolution rate, stability etc. (Haleblian and McCrone (1969): Journal of Pharmaceutical Sciences, 58:911-929).

Such properties can affect the pharmaceutical processing of the active ingredient as well as its biological availability and thus the biological efficacy (cf. Griesser (2006) in: Polymorphisms in the Pharmaceutical Industry. Hilfiker (Ed.) 211-234).

For the production of medicines, it is important that the original substance is stable, not water-drawing and controllable in its solid behavior during the complete production process. Further, the chemical stability and solid-phase stability with long storability of an active ingredient is extremely important (cf. Miller et al. (2006) in: Polymorphisms in the Pharmaceutical Industry. Hilfiker (Ed.) 385-403). It is desirable that even over a longer storing time, the physical properties of the active ingredient will be maintained. This relates, e.g., to the hygroscopicity, solubility or initial dissolution rate of the active ingredient.

U.S. Pat. No. 6,489,326 B1 describes a method for producing a 5-amino-2,3-dihydrophthalazine-1,4-dione sodium salt to be used for medical purposes, which results in a dihydrate form. The drawback of this method is the use of a heavy-metal catalyst that may leave residues in the product. Products with residues have allergenic potential and in general are deemed critical for pharmaceutical use by the EMEA (cf. Guideline EMEA/CHMP/SWP/4446/2000).

Very important for the pharmaceutical processing and the medical use are production methods, which reliably and reproducibly permit the production of the desired crystalline forms. When producing crystalline forms, it should be considered that small deviations of the process parameters will already cause changes of the crystal structure of the products and can thus finally lead to different crystalline forms or mixed forms. Properties changed thereby—for instance a modified biological efficacy by a different solubility—may lead to a rejection of complete batches, often it is not possible at all to produce the desired form (cf. Ulrich and Jones (2005): Nachrichten aus der Chemie 53:19-23). Besides the degree of purity of the active ingredient and the resulting possible changes of the efficacy, further important properties for the pharmaceutical processing can be affected in an adverse manner, e.g. the capability to be pressed to tablets by an impairment of the pourability or flow rate of the crystalline form. 5-Amino-2,3-dihydrophthalazine-1,4-dione alkali salts belong to the group of the aminophthalhydrazides and are described in prior art as immunomodulators with special anti-inflammatory, antioxidative and antitoxic properties (cf. U.S. Pat. No. 6,489,326 B1; EP 0617024, U.S. Pat. No. 5,512,573, U.S. Pat. No. 5,543,410 A, U.S. Pat. No. 7,326,690 B2).

Immunomodulatory substances are commonly grouped according to their effects into immunodepressants and immunostimulants (cf. Rote Liste Service GmbH (2011): www.rote-liste.de).

The corresponding preparations having exclusively immunodepressive or exclusively immunostimulating effect, such as for instance immunodepressive TNF alpha-blockers or immunostimulating interferon beta-preparations, often cause significant undesired side effects in the organism, exactly because of their very specific mechanism of action. Some known immunodepressive substances, such as for instance the TNF alpha-blocker adalimumab, specifically inhibit certain inflammatory mediators. Such therapies are known to have serious side effects (cf. Descotes (2008): Expert Opin. Drug Metab. Toxicol., 4: 12: 1537-1549), since the blocking of individual inflammatory mediators is a severe intervention of the complex immune system. Consequently, the organism is not capable anymore to fulfill its functions, to react automatically and physiologically appropriately to exogenous or endogenous inflammatory stimuli, such as e.g. bacterial infections. Thus, for instance, the application of TNF alpha-blockers is contraindicated in the case of serious infections, this applies in particular for sepsis and tuberculosis. Before administering a corresponding medication, such as e.g. for the treatment of rheumatoid arthritis, a TBC screening is strongly recommended (cf. Diel et al. (2009): Z Rheumatol 5:411-416). Moreover, Hoffmann (2005: Intensivmed 42:371-377) could clearly demonstrate that TNF alpha-blockers are not suitable for the clinical application in case of septic conditions, but to the contrary can even lead to an increase of mortality.

The particular immunomodulatory properties of the 5-amino-2,3-dihydrophthalazine-1,4-dione alkali salts are however distinctly useful for the prevention of so-called cytokine storms (cf. Suntharalingam et al. (2006): N Engl J Med 355; 1018-28) caused by excessive immune responses. Different from so-called cytokine blockers, these salts are mostly free from side effects, since an inhibition of individual cytokines will not take place, but these are regulated to a physiological level, and thus an adequate reaction of the organism to infectious germs is assured further on. However, prior art does not allocate any different immunospecific effects to individual crystalline forms of alkali salts for 5-amino-2,3-dihydrophthalazine-1,4-dione. In particular, no statements can be found in prior art, whether individual crystalline forms can be used specifically and according to indication, i.e. according to their basic, specific immunomodulatory main effect, preferably as immunodepressants or preferably as immunostimulants.

A special medical application of the 5-amino-2,3-dihydrophthalazine-1,4-dione sodium salt is described in the US 2003/0195183 A1 with the "Correction of the immune system" by using different doses (0.2 µg to 1,000 mg) of 5-amino-2,3-dihydrophthalazine-1,4-dione alkali salts in different experimental runs. Effective doses within this range varied depending on the examined disease and individual parameters such as e.g. species, age, gender, and weight. For instance, the application of different doses between 2 and 200 µg of 5-amino-2,3-dihydrophthalazine-1,4-dione sodium salt will lead to different consequences for the cellular immune response of mice induced by subcutaneous injection of erythrocytes (delayed hypersensitivity response—DHR). The lower is the used dose, the higher is the DHR index. In the more sensitive one of the two used mice strains, the highest dose will lead to an inhibition of the DHR. This example and further in vivo, in vitro and also clinical examples in the US 2003/0195183 A1 indicate that low doses of 5-amino-2,3-dihydrophthalazine-1,4-dione alkali salts mainly act in an immunostimulating manner, whereas higher doses of 5-amino-2,3-dihydrophthalazine-1,4-dione alkali salts mainly act in an immunodepressive manner. Since the transition from immunostimulating dose to immunodepressive dose for different mice strains is differently high, the treatment of different species and individuals in the human and veterinary medicine will also cause population-genetic effects, whereby particular risks of this dose-dependent application will result.

Therefore, for the clinical practice, in particular for the prevention of severe diseases with congenital or acquired immune deficiency or with excessive immune responses, a method for specifically controlling the immunomodulation by the simple provision of different polymorphs of a substance would be advantageous.

The property of a preferably stimulating immunomodulator is desirable for instance for the therapeutic treatment of patients having a weak immune defense, such as after an HIV infection or after a chemotherapeutic treatment.

The property of a preferably depressive immunomodulator is desirable, for instance for minimizing inflammatory processes, such as in case of a surgical operation, autoimmune diseases and allergies.

In the clinical practice, for some indications, in particular relapsing inflammatory diseases, immunostimulants as well as immunodepressants are often therapeutically used simultaneously or alternatingly (cf. DMSG 2006: Aktuelle Therapieempfehlungen September 2006; Rote Liste Service GmbH (2011): www.rote-liste.de). This will lead to an increased risk of interactions. Chemically similar substances of a substance class that are capable to produce opposite effects, would therefore offer an advantage for the clinical practice, since it can be expected that they will cause, with simultaneous or time-displaced administration, less pharmacologically caused interactions in the organism than active ingredients of different substance classes used for the same purposes.

A drawback of the prior art is further that a dose-dependent application of an immunomodulator requires higher attentiveness of the administering medical staff or of the patients themselves and thus increases the risk of application errors.

Therefore a not only dose-dependent immunospecific application of a 5-amino-2,3-dihydrophthalazine-1,4-dione alkali salt is desirable for a practical and low-risk therapeutic application, which in addition exploits the medical advantages of this substance class.

It needs to be noted that interventions in the complex rules of the immune system may have serious consequences for the involved organism. The more important for the medical application are therefore immunomodulators having as few side effects as possible and an immunologically defined effect, which makes a specific prophylaxis or therapy of immunologically caused diseases possible. Such immunomodulators would have a great importance for the medicine.

SUMMARY OF THE INVENTION

The present invention has been made on the background of the above prior art, the object of the present invention being to provide novel forms for 5-amino-2,3-dihydrophthalazine-1,4-dione sodium salt having specific, independent immunological effects that can thus be used specifically for mainly immunodepressive or mainly immunostimulating purposes. As a particularly desirable property, it is intended that these novel forms have mainly immunostimulating or mainly immunodepressive effects, respectively, independently from the dose. Furthermore, the provided forms are to have physicochemical properties, which are advantageous for medications produced, stored and/or applied therewith individually or in combination.

This object was achieved by the provision of two novel anhydrates of the 5-amino-2,3-dihydrophthalazine-1,4-dione sodium salt (anhydrate forms I and II), which surprisingly and verifiably contrast to prior art, based on experimental data in physicochemical and independent immunomodulatory properties, i.e. in particular to the known 5-amino-2,3-dihydrophthalazine-1,4-dione sodium salt. Whereas the anhydrate form I according to the invention (→crystalline form I) has immunomodulatory, in particular mainly immunostimulating properties, the novel anhydrate form II (→crystalline form II) according to the invention has immunomodulatory, in particular mainly immunodepressive properties.

The crystalline forms I and II are defined by 10 characteristic values each of interplanar spacings and 2-theta angles, expressed in one x-ray powder diffractogram each (FIGS. 2 and 3).

The inventors have found that forms I and II have positive physical properties for the pharmaceutical processing and application, including stability, storability, non-hygroscopicity and solubility. These are advantageous for the pharmaceutical production and further processing compared to for instance dihydrates, where changes of the water content and thus formulation problems may occur, e.g. by weight changes of the active ingredient during tablet pressing, encapsulation or sterilization. There are differences of physical properties between the forms according to the invention and the prior art for instance in the solubility (cf. Table 6).

Further, the inventors have set themselves the task to provide methods making the novel anhydrate forms for 5-amino-2,3-dihydrophthalazine-1,4-dione sodium salt according to the invention possible in a feasible and reproducible way. The described methods are intended to be carried out without using heavy-metal catalysts and to permit the reproducible production of the novel crystalline form II even for arbitrary batch sizes. Furthermore, the inventors have set themselves the task to provide methods for producing the crystalline forms I and II with advantageous properties with respect to pharmaceutical processing and different application types.

This object was achieved by at least one method for optionally producing crystalline form I or II, wherein sodium hydroxide and luminol are dissolved in water. By addition of a low-molecular alcohol, preferably ethanol or 2-propanol, crystalline luminol sodium salt precipitates. The desired crystalline form I or II is obtained after isolation and repeated washing steps and keeping a certain stirring time. The methods according to the invention can be used for arbitrary batch sizes.

The initial product for producing both crystalline forms is purest possible luminol or a method for producing the same by reducing 3-nitrophthalic acid in alkaline medium with a suitable reduction agent over 3-nitrophthalic anhydride. Optional purification steps by recrystallization are carried out thereafter.

The present invention finally comprises pharmaceutical preparations of forms I or II or a combination thereof, respectively alone or together with pharmaceutically suitable auxiliary substances.

Figure 1:
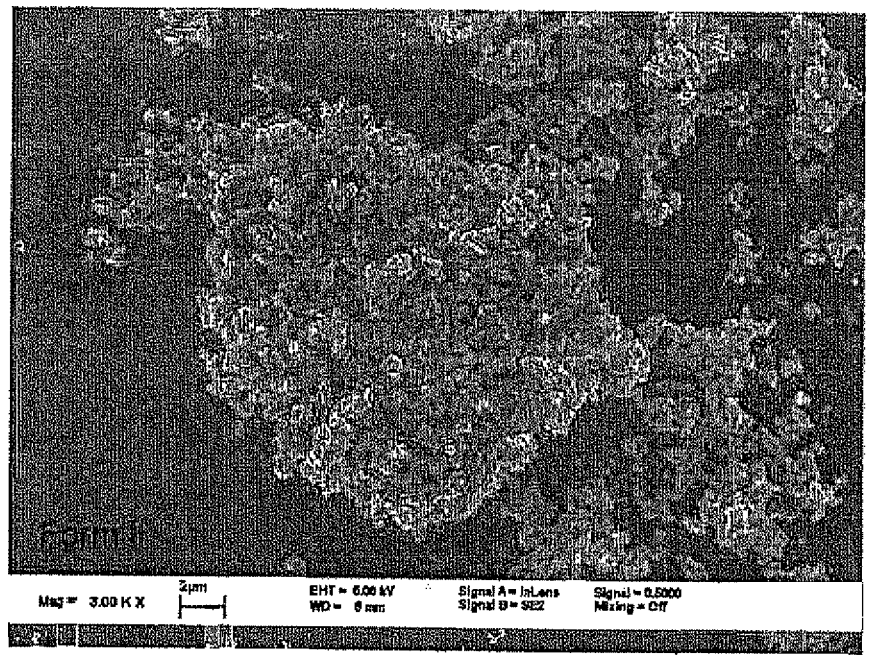
FIG. 1 shows scanning electron microscope images of form I (top) and II (bottom).
Figure 1:
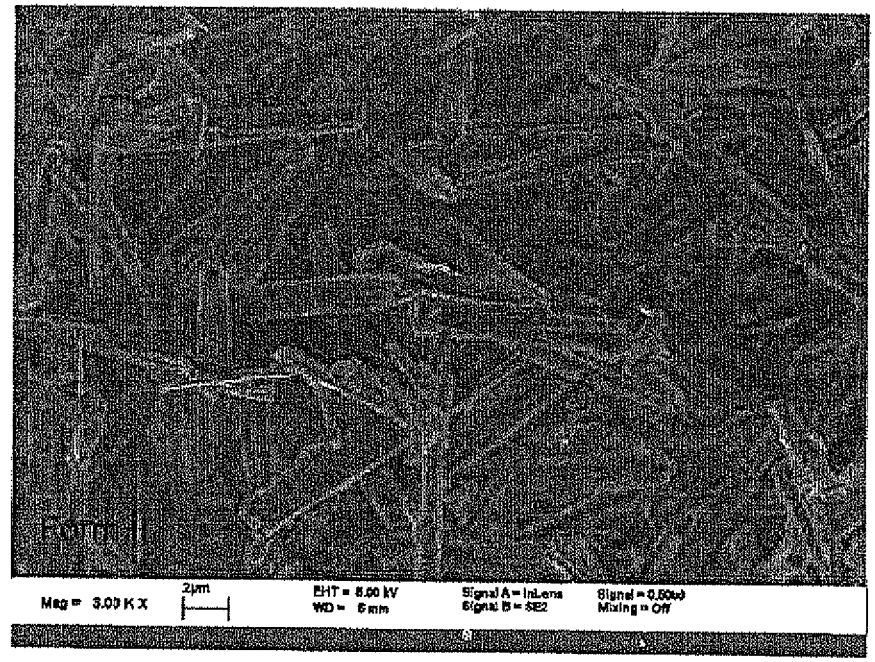
Figure 2:
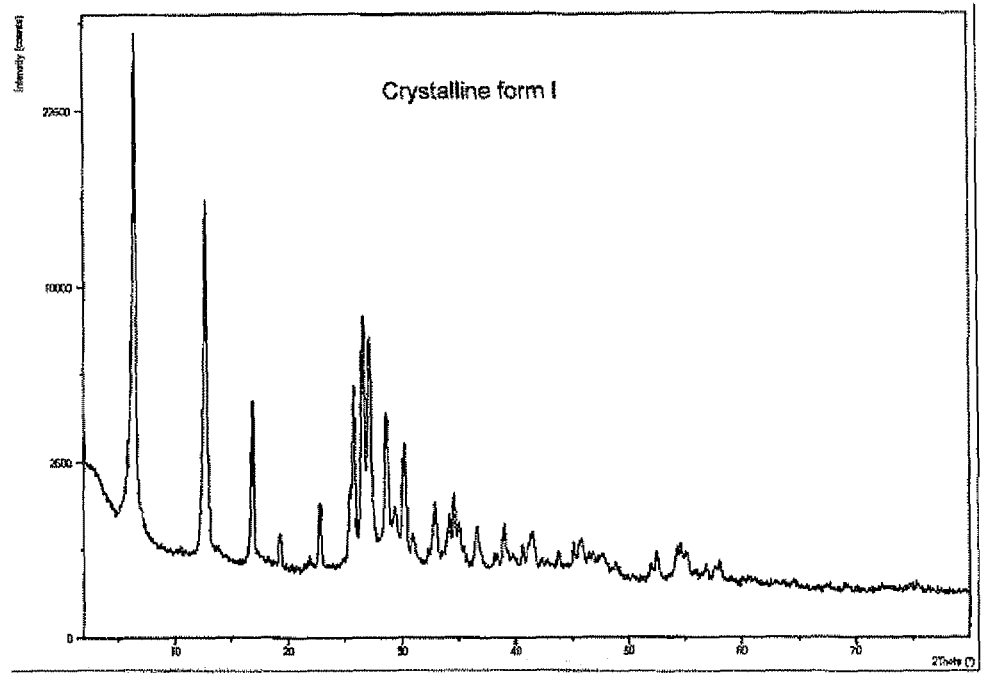
FIG. 2 describes a powder diffractogram of crystalline form I.
Figure 3:
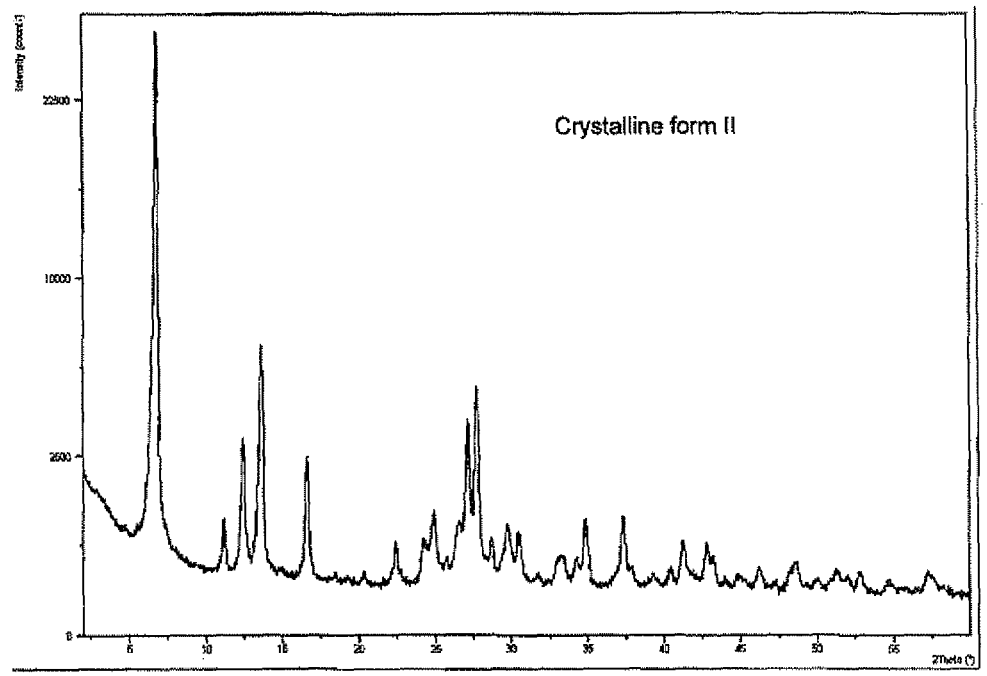
FIG. 3 describes a powder diffractogram of crystalline form II.

Form I is shown by the lower one of the two lines, form II by the upper one.

DETAILED DESCRIPTION

Unless otherwise shown, the technical and scientific terms used in the present invention have the meaning that a man skilled in the relevant technical art will attribute to them.

An "organism" is a living entity, in particular human or animal, provided with a self-regulating immunological system.

The term "active ingredient" comprises crystalline form I or crystalline form II or a mixture of both.

The term "pharmaceutical preparation" comprises the active ingredient in any pharmacologically suitable defined dose and form of administration, such as e.g. a powder, suspension, emulsion and/or mixtures thereof. It comprises pharmaceutically suitable auxiliary substances, and all substances, which are generated directly or indirectly as a combination, aggregation, complex formation of the ingredients, or as a consequence of other reactions or interactions and further other active ingredients alone or in combination.

Pharmaceutical preparations of the active ingredient according to the invention, individually or in combination with other adjuvants and standard therapies, can be formulated according to the invention in liquid and solid form and be administered in any medical acceptable way, mainly, but not exclusively, intravenously, intramuscularly, topically (e.g. eye drops), subcutaneously, transdermally, vaginally, rectally or orally, including sublingually and buccally, as well as in form of substance-eluating implants. Liquid forms may be: e.g. solutions (e.g. for injections and infusions), suspensions, emulsions, sprays, lotions and ointments. Solid forms may be: tablets, dragées, capsules, powder or other forms being familiar and appearing suitable to the man skilled in the art, e.g. suppositories.

The term "auxiliary substance" is used herein to describe every constituent of a pharmaceutical preparation besides the active ingredient itself. The choice of a suitable auxiliary substance depends on factors such as type of application and dose as well as on the influence on the solubility and stability of the preparation by the auxiliary substance itself.

Pharmaceutical "auxiliary substances" are substances that are known to the man skilled in the art or can be found in standard pharmaceutical textbooks or official pharmacopoeias (e.g. European Pharmacopoeia). Such substances may for instance have influence on the distribution of the active ingredient in different tissues and organs or change the duration of effectiveness or speed of action of medicament forms, for instance by acceleration of the resorption (for instance by dimethyl sulfoxide, nicotinic acid, hyaluronidase), or by that the start of their effectiveness is retarded by suitable retard preparations.

Pharmaceutical auxiliary substances for use in the desired form of application may for instance be: sodium citrate, calcium phosphate, calcium carbonate together with suitable tablet disintegrants, e.g. for oral application. These may for instance be substances that swell due to water uptake (starch, cellulose derivatives, alginates, polysaccharides, dextranes, cross-linked polyvinylpyrrolidone), substances that develop gas by a chemical reaction with water (sodium hydrogen carbonate, citric and tartaric acid) or substances that improve, as a hydrophilization agent, the wetting of the crystallites and thus mediate their dissolution in water (e.g. polyethylene glycol sorbitan fatty acid ester).

Auxiliary substances are also substances that can be used as binders, such as e.g. starch, gelatin, sugar substances, cellulose derivatives, or diluents, e.g. sugar substances. Further, surface-active substances, e.g. sodium lauryl sulfate or polysorbate 80, or lubricants, such as e.g. magnesium stearate, sodium stearate and further flavoring agents, antioxidants, dyers and preservation agents the man skilled in the art may find suitable.

The term "substantially pure" means a degree of purity of the active ingredient of at least 95%, preferably 98%, most preferably 99% 5-amino-2,3-dihydrophthalazine-1,4-dione sodium salt.

The term "immunospecific" designates the specific use of form I and/or form II for treating diseases with immunodeficient background or excessive immune system.

The term "effect" describes the specific, here immunospecific, mechanism of action of an active ingredient for the purpose of this invention with mainly immunostimulating or mainly immunodepressive effect.

Novel Crystalline Forms I and II for 5-amino-2,3-dihydrophthalazine-1,4-dione Sodium Salt.

The present invention includes a novel crystalline anhydrate form I of 5-amino-2,3-dihydrophthalazine-1,4-dione sodium salt characterized by an x-ray powder diffractogram of a Bragg-Brentano diffractometer (Panalytical X'Pert Pro) provided with a wavelength lambda=1.54187 Å, and with an X'Celerator Scientific RIMS detector and using a copper radiation Cu K($\alpha$1) filtered with nickel, expressed in D or 2-theta values, "D" being the interplanar spacings (Table 1) and "2-theta" being the 2-theta angles in degrees. I(rel) represents the relative intensities of the reflexes (Table 2):

TABLE 1

| D values of anhydrate form I: | | | | | | | | | | |
|---|---|---|---|---|---|---|---|---|---|---|
| | 13.51 | 6.94 | 5.24 | 4.59 | 3.89 | 3.45 | 3.35 | 3.28 | 3.11 | 2.95 |
| rounded values | 13.5 | 6.9 | 5.2 | 4.6 | 3.9 | 3.5 | 3.4 | 3.3 | 3.1 | 3.0 |

TABLE 2

| 2-theta values of anhydrate form I and relative intensities I(rel): | | | | | | | | | | |
|---|---|---|---|---|---|---|---|---|---|---|
| 2Θ | 6.5 | 12.7 | 16.9 | 19.3 | 22.8 | 25.8 | 26.6 | 27.2 | 28.7 | 30.3 |
| I/Io (rel) | vst | st | m | w | w | m | st | st | m | m | wherein:
w = weak,
m = medium,
st = strong and
vst = very strong.

The present invention further includes a novel crystalline anhydrate form II of 5-amino-2,3-dihydrophthalazine-1,4-dione sodium salt characterized by an x-ray powder diffractogram of a Bragg-Brentano diffractometer (Panalytical X'Pert Pro) provided with a wavelength lambda=1.54187 Å, and with an X'Celerator Scientific RIMS detector and using a copper radiation Cu K(α1) filtered with nickel, expressed in D or 2-theta values, "D" being the interplanar spacings (Table 3) and "2-theta" being the 2-theta angles in degrees. I(rel) represents the relative intensities of the reflexes (Table 4):

TABLE 3

| D values of anhydrate form II: | | | | | | | | | | |
|---|---|---|---|---|---|---|---|---|---|---|
| | 12.92 | 7.88 | 7.08 | 6.47 | 5.32 | 3.96 | 3.66 | 3.57 | 3.27 | 3.21 |
| rounded values | 12.9 | 7.9 | 7.1 | 6.5 | 5.3 | 4.0 | 3.7 | 3.6 | 3.3 | 3.2 |

TABLE 4

| 2-theta values of anhydrate form II and relative intensities I(rel): | | | | | | | | | | |
|---|---|---|---|---|---|---|---|---|---|---|
| 2Θ | 6.8 | 11.2 | 12.5 | 13.7 | 16.7 | 22.4 | 24.3 | 24.9 | 27.2 | 27.8 |
| I/Io (rel) | vst | w | m | st | m | w | w | w | m | st | wherein:
w = weak,
m = medium,
st = strong and
vst = very strong.

Advantageous Physical Properties:

Both forms according to the invention can be distinguished by scanning electron microscope: Form II mainly has a needle-shaped crystallite octahedral structure of several micrometers length composed of layers, whereas in the SEM of form I mainly morphologically non-uniform crystallites with rounded edges are shown that agglomerate in a powder-like manner (FIG. 1). From their crystal form result advantageous properties for pharmaceutically processing the forms according to the invention: Form II has, compared to form I, due to its crystal particle form a higher pourability and thus an improved filterability, whereas form I is better suitable, in particular due to its higher bulk density for tablet pressing, which is further promoted by its tendency to agglomeration, possibly because of the bonding of its laminar substructures.

Both crystalline forms are stable for a time of at least two months at room temperature (25° C.) and 40° C. and will only disintegrate over 335° C.±10° C. (form I) or 385° C.±10° C. (form II), respectively, whereas in the dihydrate according to U.S. Pat. No. 6,489,326 B1 an endothermous solid phase transformation can be observed already at 85° C. (Table 5). The solid phase transformation of the dihydrate according to U.S. Pat. No. 6,489,326 B1 was measured by means of the simultaneous thermogravimetry—differential thermal analysis with a Linseis L81-077 coupled with mass spectroscopy measurement with a Netzsch STA 449 C thermobalance, with MS and FTIR coupling at 30-300° C. under helium. The disintegration temperatures of forms I-II were determined with the same device at 30-500° C. in synthetic air ($4N_2:1O_2$). The data were analyzed with the factory-set software Proteus.

TABLE 5

| Disintegration temperatures of forms I-II and determination of the solid phase transformation of the dihydrate according to U.S. Pat. No. 6,489,326 B1. | | |
|---|---|---|
| Form I | Form II | Dihydrate US 6,489,326 B1 |
| 335° C. ± 10° C. | 385° C. ± 10° C. | 85° C. ± 10° C. |

The thermoanalytical data confirm the assumption of the inventors that both crystalline forms have advantageous properties with respect to stability and storability. These properties further promote the pharmaceutical processability of the crystalline forms I and II according to the invention compared to the dihydrate of the U.S. Pat. No. 6,489,326 B1 by making them insensitive to steps with high energy input, e.g. sterilization or milling.

Furthermore, both crystalline forms I and II are substantially stable with respect to a change of the water content, so that formulation problems because of changes of the active ingredient weight during the further pharmaceutical processing (e.g. tableting, encapsulating etc.) are reduced.

Further, the solubility of the crystalline forms in a saturated solution was determined. According thereto, form II is more soluble than form I; both forms are in turn clearly more soluble than the dihydrate according U.S. Pat. No. 6,489,326 B1. The novel crystalline forms represent an advantage compared to prior art, since a higher and fair maximum solubility for injection solutions permits smaller injection volumes and offers a significantly better processability for topic preparations, such as creams having low water content.

TABLE 6

Survey of the solubilities of form I and form II in water at room temperature in comparison to the dihydrate- U.S. Pat. No. 6,489,326B1 producible according to U.S. Pat. No.6,489,326 B1.

| Form I | Form II | Dihydrate/ US 6,489,326 B1 |
|---|---|---|
| 227 mg/mL | 252 mg/mL | 168 mg/mL |

Figure 4:
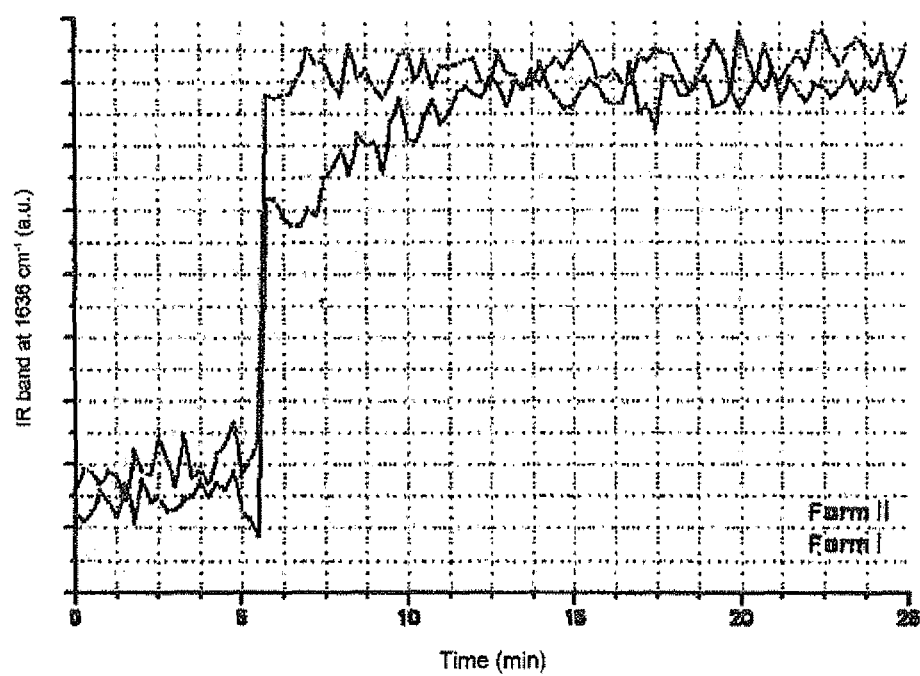
FIG. 4 describes the dissolution rate of form I and II in water as a function of time (20 min).

The comparatively better solubility of form II is also supported by the data of the initial dissolution rate. These data originate from an in-situ ATR-IR measurement in measuring intervals of 15 s each, forms I and II having been added 5 min after beginning the recording. The complete dissolution of 0.25 g form I or form II, respectively, in 10 mL $H_2O$ VE was achieved under stirring (500 rpm) at 25° C. It was found that the dissolution rate of form II in the first minutes after addition to an aqueous solution is higher than that of form I that only retarded reaches its complete equilibrium concentration. The different solubilities and initial dissolution rates of forms I and II (FIG. 4) might be caused by their different surface structures (FIG. 1). The morphologically non-uniform rounded crystallites of form I represent a tendentiously more compact surface structure than the octahedral crystals of form II that due to their shape offer solvents a larger accessible surface. The differences of the initial dissolution rates between form I and II are in particular important for producing oral formulations, since a slower dissolution rate as for form I offers advantages, where a retarded active ingredient release is intended (retard formulations). A quicker dissolution rate as for form II is advantageous for the formulation of oral acute medications, where a quickest and highest possible bioavailability is intended.

The different thermal stabilities of forms I and II are caused by the different stoichiometric coordination of the sodium cation and the luminolate molecules. Whereas in form I a sodium cation coordinates by intermolecular hydrogen bonds in total 6 luminolate molecules in a trigonal prism, there are only 4 luminolate molecules in form II, which are arranged tetrahedrally by intermolecular hydrogen bonds. Thus results a thermally tendentiously better and more stable coordination of form II than of form I.

Medical Use:

Surprisingly, the inventors found in experimental in vitro and in vivo studies a noticeably different immunological effect between crystalline forms I and II.

Further, it has been found that forms I and II can be used, due to their different immunomodulatory effect, in a more specific way than prior art: Whereas form II has an immunomodulating mainly depressive effect on certain cytokines, form I shows a mainly immunostimulating effect on certain cytokines. Form II is therefore in particular suitable for the therapeutic application under conditions with excessive immune responses, form I is in particular suitable for the therapeutic application under indications with an immunodeficient background.

In particular for chronic diseases (e.g. multiple sclerosis, hepatitis C, chronic enteritides and colitides), the immune status of the patient can always vary such that a change from immunostimulating to immunodepressive therapies or from immunodepressive to immunostimulating or a combined or time-displaced administration of both approaches appears reasonable (cf. DMSG 2006: Aktuelle Therapieempfehlungen September 2006). Therefore, the following listings can only be exemplary, the assignment of a disease to conditions with excessive immune responses does not exclude the treatment thereof with form II or with combinations of form I and form II, and the assignment of a disease to conditions with immunodeficient background does not exclude the treatment thereof with form I or with combinations of form I and form II.

Conditions with excessive immune responses are for instance rejection responses after transplantations, active autoimmune diseases (in particular active rheumatoid arthritis, relapsing multiple sclerosis, lupoid hepatitis, polyarteritis nodosa, Crohn's disease, colitis ulcerosa, dermatomyositis, Behcet's disease, uveitis, thrombocytopenic purpura, myasthenia gravis, polymyositis, psoriasis, psoriasis arthritis, Bekhterev's disease, paroxysmal nocturnal hemoglobinuria, ankylosing spondylitis, autoimmune thyreoiditis, etc.), aplastic anemia, pemphigus, pemphigoid, exogenous uveitis, nephrotic syndrome and atopic dermatitis and particularly preferably septic conditions induced by bacterial infections with Gram-negative or Gram-positive pathogens, such as e.g. by MRSA (methicillin-resistant *Staphylococcus aureus*) and systemic inflammatory response syndrome (SIRS) induced by other (e.g. immunological or chemical) factors.

Conditions with immunodeficient background are for instance frequent flues, relapsing respiratory tract infections, relapsing infections of the efferent urinary tract, fatigue, weakness, absent-mindedness of unknown genesis, reconvalescence, chronic virus infections (in particular HIV, hepatitis B, hepatitis C, enzephalitis, herpes zoster, herpes simplex, infections of the inner ear, varicella, measles, cytomegaly, Epstein-Barr), different oncologic diseases (in particular hairy cell leukemia, myeloid leukemia, multiple myeloma, follicular lymphomas, Kaposi's sarcoma, cutaneous T-cell lymphoma, nasopharyngeal carcinoma, carcinoid, renal cell carcinoma, urinary bladder carcinoma, basal-cell carcinomas, metastatic carcinomas and particularly preferably malignant melanoma), septic granulomatosis, neutropenia, genital warts, keratoses, autoimmune diseases (in particular non-active stages, such as for instance relapsing multiple sclerosis between the exacerbations), radiogenic colitis, diverticulitis, allergies (in particular hay fever, polymorphous light eruption, eczema, neurodermitis), enteritis, colitis, as well as particularly preferably accompanying before, during and after chemotherapies and radiation therapies.

Surprisingly, the inventors could show different effects by the simple provision of specific crystal forms of the 5-amino-2,3-dihydrophthalazine-1,4-dione sodium salt, preferably of polymorphs of the anhydrate, particularly preferably of form I and form II. These different effects permit a specific immunomodulatory application for mainly immunostimulating (form I) or mainly immunodepressive (form II) purposes, both forms generally acting in a regulating manner on the immune system. Thus, the inventors could prove in vitro and in vivo a surprising immunostimulating effect for form I.

Form II in contrast has immunomodulatory properties that are advantageous for activated macrophages. The inventors could in particular substantiate mainly immunodepressive properties of form II based on in vitro tests with LPS-stimulated macrophages. Hereby, a distinct reduction of the IL-6 values was achieved. By in vivo tests of mice (sepsis model with S. pyogenes), a considerable therapeutic efficacy of form II could also be verified.

Furthermore, the inventors could show by the weight development and the liver enzyme values of healthy mice that the novel forms I and II do not have any or only a low toxicity. Both forms act in an immunomodulatory way, without being exclusively immunostimulating or exclusively immunodepressive. Form I as well as form II lead to higher survival rates in the sepsis model.

The inventors assume that a combined, preferably time-displaced application of form I and form II may also be successful, and that for certain indications, in particular but not exclusively autoimmune diseases, a combined application is advantageous over the individual application.

EXAMPLE 1

Effect of Form I on LPS-Stimulated Murine Macrophages In Vitro

In a test with isolated mouse macrophages, the immunomodulatory effect of form I was to be shown in vitro based on the concentration of TNF-alpha or IL-6 measured in the supernatants. For this purpose, the macrophages were first treated with form I (20 or 200 μg/mL). After 1 hour the treated macrophages were stimulated with LPS (10, 100 or 1,000 ng/mL). The supernatants were collected 24 h later, and the concentration of TNF-alpha and IL-6 was measured. Not stimulated macrophages, not stimulated macrophages treated with 200 μg/mL form I and LPS-stimulated macrophages (10, 100 or 1,000 ng/mL LPS) were used as controls. The measured values are listed in Table 7.

With sole administration of LPS (in concentrations of 1 μg/mL, 100 ng/mL and 10 ng/mL), the TNF-alpha measurements of Table 7 show a dose-dependent stimulation by LPS.

TABLE 7

|  | Dose | LPS | N | TNF-alpha (ng/mL) MW | STD | IL-6 (ng/mL) MW | STD |
| --- | --- | --- | --- | --- | --- | --- | --- |
| Form I | 20 μg | 1 mg/mL | 6 | 47.91 | 3.89 | 22.67 | 2.21 |
|  | 200 μg | 1 mg/mL | 6 | 32.53 | 4.44 | 15.95 | 3.84 |
|  | 20 μg | 100 ng/mL | 6 | 27.17 | 4.77 | 19.67 | 3.76 |
|  | 200 μg | 100 ng/mL | 6 | 16.47 | 4.07 | 10.88 | 2.09 |
|  | 20 μg | 10 ng/mL | 6 | 13.27 | 5.99 | 6.05 | 4.30 |
|  | 200 μg | 10 ng/mL | 6 | 20.74 | 7.57 | 7.19 | 5.56 |
| Control I (not stimulated) |  |  | 3 | 0.00 | 0.00 | 0.00 | 0.00 |
| Control II (200 μg/mL form I) | 200 μg/mL |  | 6 | 7.98 | 6.53 | 0.24 | 0.41 |
| Control III (1 μg/mL LPS) |  | 1 μg/mL | 3 | 50.97 | 6.59 | 28.62 | 2.07 |
| Control III (100 ng/mL LPS) |  | 100 ng/mL | 3 | 32.32 | 2.10 | 26.97 | 4.42 |
| Control III (10 ng/mL LPS) |  | 10 ng/mL | 3 | 25.36 | 5.61 | 27.70 | 4.02 |

In the combination groups with LPS and with form I-treated macrophages, in all LPS groups could be seen a dose-dependent, immunodepressive effect of form I. This effect was most distinct in the combination with 100 ng/5 mL macrophages stimulated with LPS and treated with 200 μg/mL form I, followed by a significant reduction of TNF-alpha values in the combination of 1 μg/mL LPS with 200 μg/mL form I.

Besides, in the control group of the not stimulated macrophages treated with 200 μg/mL form I could be seen, as proved by the measured TNF-alpha values, a distinct immunomodulatory, here immunostimulating effect.

EXAMPLE 2

Effect of Form II on LPS-Stimulated Murine Macrophages In Vitro

In a further in vitro model with bone marrow macrophages (mouse), the immunomodulatory, mainly immunodepressive treatment effect of form II could be confirmed. For this purpose, isolated mouse bone marrow macrophages were first treated with form II in concentrations of 2, 20 or 200 μg/mL and stimulated 1 h after treatment with 100 ng/mL or 10 ng/mL LPS. The supernatants were collected 24 h later, and the concentration of TNF-alpha and IL-6 was measured. Not stimulated macrophages, not stimulated macrophages treated with 200 μg/mL form II and LPS-stimulated macrophages (10 or 100 ng/mL LPS) were used as controls. The measured values are listed in Table 8.

TABLE 8

|  | Dose | LPS | N | TNF-alpha (ng/mL) MW | STD | IL-6 (ng/mL) MW | STD |
| --- | --- | --- | --- | --- | --- | --- | --- |
| Form II | 2 μg | 100 ng/mL | 7 | 7.40 | 3.49 | 2.67 | 0.76 |
|  | 20 μg | 100 ng/mL | 9 | 9.06 | 1.36 | 4.28 | 0.54 |

TABLE 8-continued

|  | Dose | LPS | N | TNF-alpha (ng/mL) | | IL-6 (ng/mL) | |
| --- | --- | --- | --- | --- | --- | --- | --- |
|  |  |  |  | MW | STD | MW | STD |
|  | 200 µg | 100 ng/mL | 9 | 7.69 | 1.62 | 4.00 | 1.20 |
|  | 2 µg | 10 ng/mL | 9 | 8.38 | 1.76 | 3.93 | 1.01 |
|  | 20 µg | 10 ng/mL | 9 | 9.80 | 0.72 | 1.61 | 1.30 |
|  | 200 µg | 10 ng/mL | 6 | 6.76 | 1.60 | 3.42 | 1.29 |
| Control (not stimulated) |  |  | 9 | 0.00 | 0.00 | 0.00 | 0.00 |
| Control (not stimulated) | 200 µg |  | 9 | 0.00 | 0.00 | 0.00 | 0.00 |
| Control |  | 100 µg/mL | 9 | 12.46 | 1.70 | 4.47 | 1.67 |
| Control |  | 10 ng/mL | 9 | 9.45 | 1.47 | 3.19 | 1.33 |

A significant reduction of the TNF-alpha concentration could be measured in the group of the macrophages stimulated with 100 ng/mL LPS in all active ingredient concentrations. In the group of the macrophages stimulated with 10 ng/mL LPS a significant reduction of TNF-alpha in the highest active ingredient concentration (200 µg/mL) could be seen.

An immunodepressive effect of form II on LPS-stimulated macrophages could furthermore be observed based on significant reductions of IL-6 values. These were measured in the combination of 2 µg/mL active ingredient with macrophages stimulated with 100 ng/mL LPS as well as in the group of the macrophages stimulated with 10 ng/mL in the active ingredient concentration with 20 µg/mL. These results are in accordance with IL-6 values from an earlier in vitro pilot test with macrophages, in which a different LPS and active ingredient combination (1 µg/mL LPS with 100 µg/mL) was used and which also showed an immunodepressive effect of form II on stimulated murine macrophages. An immunostimulating effect on not LPS-induced macrophages could not be shown.

EXAMPLE 3

Weight Development of Healthy Mice

In a mouse model of the Gram-positive sepsis (infection with *S. pyogenes*) the therapeutic usability of the crystal forms I and II of the 5-amino-2,3-dihydrophthalazine-1,4-dione sodium salt was tested. The administration of active ingredient was made parenterally 6 hours after the infection occurred. A second administration of active ingredient was made 24 hours after the first application. The test was completed 48 hours after the infection. For both forms (substance groups) three different doses were used. The mice obtained 2, 20 or 200 µg each of form I or form II per animal and application.

Besides the substance groups (form I and form II) one group obtained a common salt solution (NaCl) instead of the dissolved active substances, and one group did not receive any treatment. In parallel to the infected animals, comparable groups with not infected animals were formed.

The individual treatment groups comprised 5 animals each, and for the not infected controls two repetitions and for the infected controls and that groups that contained form II four repetitions were made, so that in total 180 animals were in the test.

It is known that the toxicity of substances in an animal test with growing-up mice or rats can influence the weight development. The weight development (g) of the not infected control animals over a time of two days is summarized in Table 9.

TABLE 9

|  | Dose | N | Weight development/MW | increase (g) STD |
| --- | --- | --- | --- | --- |
| Form I | (total) | 15 | 0.59 | 1.33 |
|  | 2 µg | 5 | −0.49 | 0.81 |
|  | 20 µg | 5 | 1.48 | 1.58 |
|  | 200 µg | 5 | 0.79 | 0.73 |
| Form II | (total) | 30 | 0.59 | 2.19 |
|  | 2 µg | 10 | −0.14 | 1.79 |
|  | 20 µg | 10 | 1.43 | 2.14 |
|  | 200 µg | 10 | 0.50 | 2.52 |
| NaCl | — | 10 | 0.67 | 1.87 |
| Control | — | 10 | 0.68 | 1.93 |
| Total | — | 65 | 0.62 | 1.89 |

There were no deaths among the not infected animals. Relevant differences of the weight development between the groups could not be found. It can therefore be assumed that form I as well as form II do not have any toxicity or at most a very small one.

EXAMPLE 4

Weight Development of Infected Mice

In the sepsis model described in Example 3, the influence of crystal forms I and II of the 5-amino-2,3-dihydrophthalazine-1,4-dione sodium salt on the weight development of mice infected with *S. pyogenes* was tested. The development of the body weight during an acute infection may supply important predictive information. Some animals did not survive the second day till the end of the test. Tendentiously, the body weight development of the individual during the first 24 hours after the infection gave a hint for the probability to survive till the end of the test after 48 hours, there was however no significant correlation. Since there do not exist data about the weight development over the full test time for the animals having died during the second day, there is also shown in the following Table 10, in addition to the weight development for the complete test time, the weight development of the first test day.

TABLE 10

|  |  | Weight development/increase (g) | | | | | |
| --- | --- | --- | --- | --- | --- | --- | --- |
|  |  | Day 1 | | | Total | | |
|  | Dose | N | MW | STD | N | MW | STD |
| Form I | (total) | 15 | −0.25 | 0.39 | 12 | −1.85 | 0.54 |
|  | 2 µg | 5 | −0.64 | 0.21 | 4 | −2.41 | 0.37 |
|  | 20 µg | 5 | −0.09 | 0.31 | 4 | −1.46 | 0.28 |
|  | 200 µg | 5 | −0.03 | 0.32 | 4 | −1.69 | 0.47 |
| Form II | (total) | 60 | −0.62 | 1.56 | 48 | −1.86 | 1.65 |
|  | 2 µg | 20 | −0.57 | 1.86 | 18 | −2.02 | 1.34 |
|  | 20 µg | 20 | −0.55 | 1.56 | 16 | −1.69 | 0.85 |
|  | 200 µg | 20 | −0.72 | 1.28 | 14 | −1.86 | 2.56 |
| NaCl | — | 20 | −0.68 | 1.43 | 14 | −1.77 | 1.89 |
| Control | — | 20 | −0.50 | 2.16 | 11 | −1.85 | 1.21 |
| Total | — | 115 | −0.56 | 1.55 | 85 | −1.84 | 1.51 |

Tendentiously, the mice that obtained form I of the 5-amino-2,3-dihydrophthalazine-1,4-dione sodium salt showed lower weight losses in the first 24 hours after the infection than the animals in the control groups. This advantage is particularly significant for the doses 20 and 200 µg of form I. This indirect hint on a tendentiously higher survival rate in the substance groups cannot be found anymore for the animals that survived the second day.

EXAMPLE 5

Probability of Survival After *S. pyogenes* Infection

In the sepsis model described in Example 3, the influence the crystal forms II and I of the 5-amino-2,3-dihydrophthalazine-1,4-dione sodium salt on the probability of survival of the mice infected with *S. pyogenes* was tested. The individual groups showed different probabilities to survive at least 48 hours after the infection. The shares of the surviving animals are summarized in Table 11.

TABLE 11

|  | Dose | N | Share of surviving mice (%) |
|---|---|---|---|
| Form I | (total) | 15 | 80 |
|  | 2 µg | 5 | 80 |
|  | 20 µg | 5 | 80 |
|  | 200 µg | 5 | 80 |
| Form II | (total) | 60 | 80 |
|  | 2 µg | 20 | 90 |
|  | 20 µg | 20 | 80 |
|  | 200 µg | 20 | 70 |
| NaCl | — | 20 | 70 |
| Control | — | 20 | 55 |
| Total | — | 115 | 74 |

Form I and form II both lead to an increase of the share of surviving animals compared to the controls. Thus, a positive influence on the septic behavior can be assumed for form I as well as for form II, also independently from its respective specific effect.

EXAMPLE 6

Germ Load in Blood and Liver

In the sepsis model described in Example 3, the influence of crystal forms II and I of the 5-amino-2,3-dihydrophthalazine-1,4-dione sodium salt on the germ load of the mice infected with *S. pyogenes* in blood and liver was tested. The test was completed hours after the infection, and the germ load (CFU) existing at this time in blood and liver was determined (see Table).

TABLE 12

|  |  | Germ load (CFU) | | | | | |
|---|---|---|---|---|---|---|---|
|  |  | Blood (log/mL) | | | Liver (log/g) | | |
|  | Dose | N | MW | STD | N | MW | STD |
| Form I | (total) | 12 | 6.37 | 1.20 | 12 | 6.41 | 0.65 |
|  | 2 µg | 5 | 7.00 | 1.49 | 4 | 6.56 | 0.97 |
|  | 20 µg | 5 | 6.33 | 1.06 | 4 | 6.57 | 0.37 |
|  | 200 µg | 5 | 5.77 | 0.94 | 4 | 6.09 | 0.55 |
| Form II | (total) | 46 | 5.80 | 1.37 | 47 | 6.36 | 1.52 |
|  | 2 µg | 16 | 5.96 | 1.21 | 17 | 6.13 | 1.69 |
|  | 20 µg | 16 | 5.88 | 1.65 | 16 | 6.79 | 0.76 |
|  | 200 µg | 14 | 5.54 | 1.26 | 14 | 6.14 | 1.91 |
| NaCl | — | 14 | 6.39 | 1.42 | 14 | 6.20 | 1.83 |
| Control | — | 2 10? | 6.50 | 1.03 | 10 | 6.86 | 0.55 |
| Total | — | 82 | 6.07 | 1.33 | 83 | 6.40 | 1.40 |

Form II as well as form I showed in the highest dose a tendentious germ count reduction in the blood compared to the controls. The inventors regard this as evidence of a better controllability of the infection by the administration of 5-amino-2,3-dihydrophthalazine-1,4-dione sodium salt, in particular form 2. It should be noted however that for animals having died before the end of the test, there are no germ count determinations. The inventors assume that for a germ count determination at an earlier time the germ load of the animals having died later would have been particularly high, and thereby the effects induced by forms I and II would be even more apparent.

EXAMPLE 7

Cytokines in Healthy Test Animals

When administering form I and form II to healthy mice, it was investigated for the animal model described in Example 3, whether and which influence the application has on certain cytokines, in particular IL-6 and TNF-alpha, in mice. Blood taking occurred after 48 hours at the end of the second application day. For IL-6, neither in the substance groups nor in the control groups increases could be found. The results for TNF-alpha are summarized in Table 13.

TABLE 13

|  |  |  | TNF-alpha | (pg/mL) |
|---|---|---|---|---|
|  | Dose | N | MW | STD |
| Form I | (total) | 15 | 208.2 | 219.4 |
|  | 2 µg | 5 | 128.8 | 137.2 |
|  | 20 µg | 5 | 341.8 | 209.6 |
|  | 200 µg | 5 | 154.1 | 268.2 |
| Form II | (total) | 30 | 5.65 | 30.93 |
|  | 2 µg | 10 | 0.0 | 0.0 |
|  | 20 µg | 10 | 0.0 | 0.0 |
|  | 200 µg | 10 | 16.94 | 53.58 |
| NaCl | — | 10 | 23.66 | 74.81 |
| Control | — | 10 | 0.0 | 0.0 |
| Total | — | 65 | 54.3 | 137.93 |

Whereas form II and the controls do not cause a relevant increase of TNF-alpha, distinct increases compared to the other groups occurred after the administration of form I. This effect was most distinct for the 20 µg dose, this group was significantly different ($p<0.001$) from the control groups as well as from the groups that received form II. Here, a specific immunostimulating effect occurs for form I that cannot be detected for form II.

EXAMPLE 8

Cytokines in the Sepsis Model

In the sepsis model described in Example 3, it was also investigated, which influence the administration of form I and form II has on certain cytokines, in particular IL-6 and TNF-alpha, in mice infected with *S. pyogenes*. Blood taking occurred at the end of the test 48 hours after the infection.

Since it could be shown that the cytokine increases caused by the infection are significantly different, in some cases even within the control groups (negative control and NaCl) between the repetitions, the data from the repetitions could not be amalgamated.

It should further be noted that these values were only obtained for those animals that also survived the second test day till the end. The inventors furthermore assume that the animals that have died previously had very high prognostically unfavorable IL-6 values.

Nevertheless, there were in part distinct tendencies of an IL-6 reduction by form II, could however unfortunately not be confirmed in all repetitions. Further animal models that are better suitable to absolutely prove the depressive effect of form II on cytokines even in vivo, are at present investigated by the inventors.

EXAMPLE 9

Liver Enzymes/Transaminases for Healthy Test Animals

When administering form I and form II to healthy mice, it was investigated, whether and which influence the application has on certain liver enzymes, in particular the transaminases GOT (AST) and GPT (ALT). Blood taking occurred at the end of the second application day. Distinct differences between the groups could not be found here. This confirms the good compatibility shown in Example 3.

EXAMPLE 10

Liver Enzymes/Transaminases in the Sepsis Model

In the sepsis model described in Example 3, it was also investigated, which influence the administration of form I and form II has on certain liver enzymes, in particular the transaminase GOT (AST) and GPT (ALT), in mice infected with S. pyogenes.

Blood taking occurred 48 hours after the infection. For an infection with septic course, in some cases drastic increases of the liver enzyme values may occur. In an analogous manner as for the cytokine values of the infected mice, significant differences within identical groups occurred here, too, between the individual repetitions, so that an overall analysis of the data was not possible. Form II showed in some repetitions tendencies to reduce the liver enzyme values. These hints could however not be seen in all repetitions.

Substantial differences between the groups could however not be found. In an analogous manner as for the germ counts in Example 6 and the cytokine values in Example 8, there is a bias by the missing data of animals prematurely having died. The inventors assume that a determination of the transaminases after 24 hours would be a distinct advantage for the mice treated with 5-Amino-2,3-dihydrophthalazin-5 1,4-dione sodium salt, in particular form II.

Production of the Crystalline Anhydrate Forms I and II According to the Invention.

In the following, the production of the crystalline forms I and II is exemplarily described.

The starting point of the synthesis for all production examples is luminol known from prior art, which can for instance be produced according to the following reaction scheme:

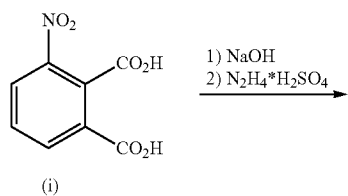

(i)

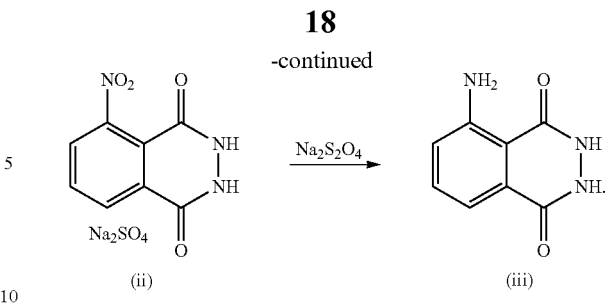

Here is shown the synthesis of luminol (iii) by reaction of 3-nitrophthalic acid (i) that can be reduced in alkaline medium by hydrazine or one of its salts, or other suitable reduction agents, for instance ammonium sulfite or triethylene glycol, to luminol via 3-nitrophthalic anhydride (ii). Suitable production methods for luminol can be found in: Williamson, K. L. In: Macroscale and Microscale Organic Experiments; 2nd ed.; D. C. Heath: Lexington, Mass., 1994. Another method suitable for producing luminol, which utilizes a Raney nickel catalyst, is for instance found in the U.S. Pat. No. 6,489,326 B1.

In a more specific method, the starting product luminol can also be produced as follows, and using the specified equivalents, arbitrary quantities of luminol can be produced:

Production Example Luminol.

1$^{st}$ Step: 3-nitrophthalic acid-3-nitrophthalhydrazide

Batch Sizes:

| Substance | Equivalents | Batch | Quantity [mol] |
|---|---|---|---|
| 3-Nitrophthalic acid | 1 | 200 g | 0.95 |
| Hydrazine hydrate (98%) | 1.1 | 51 g (50 mL) | 1.02 |
| Ethylene glycol | 1.5 (vol/m) | 300 mL | N/A |
| Water | 6 (vol/m) | 1200 mL | N/A |
| Water for washing | 3 × 1.5 (vol/m) | 900 mL (3 × 300 mL) | N/A |

In a first step, 3-nitrophthalic acid (200 g, 0.95 mol) and hydrazine hydrate (51 g, 1.02 mol) were provided and mixed with ethylene glycol (300 mL) in a 2 l reaction flask equipped with a combination of a reflux condenser (T=110° C.) and a Liebig condenser. The temperature was increased to 110° C., and the water was removed by distillation. Heating of the reaction mixture was continued up to reflux of the ethylene glycol at approx. 200° C. After one hour no more water was formed. The mixture was cooled to approx. 100° C., and water (1200 mL) was added. A lightly brownish precipitate was generated. The mixture was cooled by addition of icy water to room temperature (25° C.±5° C.) and stirred over night. The precipitate was filtered and washed with water (3×300 mL). The moist product was dried at the rotary evaporator at 90° C./20±10 mbar until constant masses were obtained.

The advantages of this method are that by the use of hydrazine hydrate instead of hydrazine sulfate, there will not be formed any disturbing inorganic material in the following steps, and that by using ethylene glycol with a boiling point of approx. 196° C. the process control by reflux boiling can be better handled than by other solvents with higher boiling points, the use of which could lead to contaminations in the product.

2$^{nd}$ Step:3-nitrophthalhydrazide-5-amino-2,3-dihydrophthalazine-1,4-dione

Batch Sizes:

| Substance | Equivalents | Batch | Quantity [mol] |
|---|---|---|---|
| 3-Nitrophthalhydrazid | 1 | 100 g | 0.48 |
| Sodium dithionite | 3.6 | 300 g | 1.73 |
| NaOH (3M) | 17 (vol/m) | 1,700 mL | N/A |
| Acetic acid | 7.2 | 200 mL (210 g) | 3.5 |
| Water for washing | 3 × 1.5 (vol/m) | 510 mL (3 × 170 mL) | N/A |

In a second step, 3-nitrophthalhydrazide was reacted to 5-amino-2,3-dihydrophthalazin-1,4-dione by that 3-nitrophthalhydrazide (100 g, 0.48 mol) 48.3 mmol) is dissolved in 3 molar sodium hydroxide solution (1,700 mL) while heating to approx. 50-60° C. To this solution the sodium dithionite (300 g, 1.73 mol) is added in portions. Thereby, the temperature of the reaction mixture will rise to approx. 80° C. After complete addition of sodium dithionite, the reaction mixture is heated for approx. 4 h for reflux. Acetic acid (200 mL, 1.73 mol) is added, and the reaction mixture is cooled down over night. The resulting precipitate is isolated and washed with water (3×170 mL). The product is dried at the rotary evaporator at approx. 80° C./20±10 mbar.
Anhydrate Form I.

I. Production Example I

Crystalline Form I

Subject matter of the invention is a method for producing the anhydrate form I by mixing 5-amino-2,3-dihydrophthalazine-1,4-dione (luminol) in sodium hydroxide solution and adding this solution dropwise to a low-molecular liquid alcohol, preferably ethanol that lowers the solubility product of the generated luminol sodium salt such that the latter will start to precipitate. The alcohols should have a degree of purity of preferably ≥95%, particularly preferably ≥98%. According to the invention, the generated precipitate is dried at temperatures between 50 and maximum 90° C.

Production Example I

Crystalline Form I—Embodiment I

In a preferred embodiment of production example I, crystalline form I can be precipitated by mixing 500-750 mL of a 0.8-1.2 molar luminol suspension with 500-750 mL of a 1.0-1.3 molar soda solution, the mixture being added dropwise at 20-50° C. under stirring to 10-15 l of a low-molecular alcohol, preferably ethanol, preferably with a degree of purity ≥95%, particularly preferably ≥98%, and the suspension being then stirred for 15-25 h at 10-40° C. After isolation, the generated precipitate is then preferably air dried. After further drying at 50° C.-80° C., the precipitate is dissolved in a 10-20-fold quantity of a low-molecular alcohol, preferably ethanol with a degree of purity ≥95%, particularly preferably ≥98%, and the suspension is stirred and filtered for 15-25 h at 10-40° C. The filter cake is then air dried, redried at 50° C.-90° C., preferably 50° C., pulverized and dried until a content of water of crystallization of ≤0.4%, preferably ≤0.3%, most preferably ≤0.2%, is achieved.

Production Example I

Crystalline Form I—Embodiment II a) In a particularly preferred embodiment of production example I, crystalline form I can be produced as follows:
b) Provide 190-220 g luminol in the 2 l beaker and dissolve it under stirring at least at 20° C. in 1.25 L 1.0-1.1 molar NaOH solution.
c) Filter batch solution through the porcelain funnel with filter paper Ø70 mm (e.g. Schleicher & Schuell Type 1575), without rewashing.
d) Provide 12-14 l ethanol (preferably with a degree of purity ≥98%) in the 3-neck bottom flask. Add batch solution dropwise under stirring at 25° C.±10° C. within 25 min±10 min. Stir suspension for 16±5 h at 20° C.±10° C.
e) Filter precipitate through a porcelain funnel with filter paper and rewash with approx. 400-500 mL of a low-molecular alcohol, preferably ethanol with a degree of purity ≥98%.
f) Finely disperse filter cake on a glass bowl and dry under the exhaust hood over night. Then re-dry in the compartment drier at 50° C.-90° C., preferably 50° C.-70° C., particularly preferably 50° C., until constant masses are obtained.
g) Pulverize and weigh precipitate.
h) Provide the 12-15-fold quantity (12-15 mL/g) of the obtained precipitate of g) at a low-molecular alcohol (e.g. methanol, ethanol, 2-propanol, preferably with a degree of purity ≥98%) in a 4 l 3-neck bottom flask. Suspend the precipitate therein under stirring. Stir the suspension for 16 h±5 h at 20° C.±10° C. Filter the suspension through a porcelain funnel with filter paper and rewash with approximately 500 mL of a low-molecular alcohol.
i) Finely disperse the filter cake on a glass bowl and dry it under the exhaust hood over night. Then dry it in the compartment drier for 2-6 h at 50° C.-70° C., preferably 50° C., until constant masses are obtained. Grind the substance using a mortar and weigh it. The content of water of crystallization should be ≤0.4%, measured according to e.g. the Karl-Fischer titration method. If the content of water of crystallization is >0.4%, repeat steps h)-i).
j) Weigh the substance and determine yield.

Production Example I

Crystalline Form I—Embodiment III

In a most preferred embodiment, crystalline form I can be produced as follows:
a) Provide 200 g luminol in the 2 l beaker and dissolve under stirring at 30° C.±10° C. in 1.25 liter 1 molar NaOH solution.
b) Filter batch solution through the porcelain funnel with filter paper Ø70 mm (e.g. Schleicher & Schuell Type 1575) without rewashing.
c) Provide 12.5 l ethanol, preferably with a degree of purity ≥99%, in the 20 l 3-neck bottom flask. Add the batch solution dropwise under stirring at 25° C.±5° C. within 30 min±5 min. Stir the suspension for 20 h±1 h at 25° C.±5° C.
d) Filter the suspension through a porcelain funnel with filter paper Ø185 mm (e.g. Schleicher & Schuell Type 1575) and rewash with approx. 500 mL ethanol, preferably with a degree of purity ≥99%. Finely disperse the filter cake on a glass bowl and dry it under the exhaust hood. Then dry in the compartment drier at 50° C.-70° C., preferably 50° C., until constant masses are obtained.
e) Pulverize the precipitate and weigh it.

f) Provide the 12-fold quantity (12 mL/g) of the obtained precipitate of ethanol, preferably with a degree of purity ≥99%, in the 3-neck bottom flask. Suspend the substance therein under stirring. Stir the suspension for 20 h±1 h at 25° C.±5° C. Filter the suspension through a porcelain funnel with filter paper Ø185 mm (e.g. Schleicher & Schuell Type 1575) and rewash with approx. 500 mL ethanol with a degree of purity of ≥95%, preferably ≥98%. Finely disperse the filter cake on a glass bowl and dry it under the exhaust hood. Then dry in the compartment drier at 50° C.-70° C., preferably 50° C. until constant masses are obtained. Grind the product using a mortar and weigh it.

g) The content of water of crystallization should be ≤0.4%, measured e.g. by Karl-Fischer titration. If the content of water of crystallization is >0.4%, repeat steps f)-g).

h) Weigh substance and determine yield.

Production Example II

Crystalline Form I

Under aqueous conditions, starting from luminol, crystalline form I can be produced by that a sodium hydroxide solution is prepared, to which the luminol is added. The luminol is dissolved by stirring. Then, ethanol is added within 10-40 min, the luminol precipitating as a salt. After complete addition and stirring for several hours, the suspension is filtered, the filter cake is washed and dried.

Production Example II

Form I—Embodiment II

In a preferred embodiment, crystalline form I is produced using the following equivalents of reactants: A solution of 1.0-1.4 equivalents sodium hydroxide in 4-7 vol/m water is prepared, to which 1 equivalent luminol is added. The reaction mixture is stirred until complete dissolution is achieved. Then, ethanol (50-70 vol/m) is added dropwise at room temperature (25° C.±5° C.) within approx. 10-40 min. The luminol sodium salt precipitates as a sediment.

After complete addition, the reaction mixture is restirred for several hours at room temperature (25° C.±5° C.), and the suspension is filtered; the filter cake is washed with ethanol (approx. 10-15 vol/m) and optionally dried in the vacuum compartment drier or at a rotary evaporator.

Production Example II

Form I—Embodiment III

In a particularly preferred embodiment, crystalline form I is produced using the following equivalents of reactants:

| Substance | Equivalents | Batch | Quantity [mol] |
|---|---|---|---|
| Luminol | 1 | 82 g | 0.46 |
| Sodium hydroxide | 1.2 | 22 g | 0.55 |
| Water for luminol solution | 6 (vol/m) | 490 mL | N/A |
| Ethanol abs. | 60 (vol/m) | 4,900 mL | N/A |
| Ethanol abs. for washing | approx. 13 (vol/m) | 1,050 mL (3 × 350 mL) | N/A |

A solution of 1.0-1.4 equivalents sodium hydroxide, preferably 1.2 equivalents sodium hydroxide (22 g, 0.55 mol), in water (6 vol/m) is produced (10 l reactor).

1 equivalent luminol is added to the sodium hydroxide solution. The reaction mixture is stirred until complete dissolution is achieved. A brown clear solution results.

Then, ethanol (60 vol/m) is added dropwise at room temperature (25° C.±5° C.) within approx. 20 min. The luminol sodium salt precipitates as a sediment.

After complete addition, the reaction mixture is restirred for maximum 20 h, preferably 2-8 h, particularly preferably 8 h at room temperature (25° C.±5° C.), and the suspension is filtered; the filter cake is washed with ethanol (approx. 13 vol/m) and optionally dried in the vacuum compartment drier at 50-90° C./1-3 mbar, preferably 50-70° C., particularly preferably 50° C., or at a rotary evaporator at 20±10 mbar and 50° C.-90° C., preferably 50°-70° C., particularly preferably 50° C.

Production Example III

Form I—Scalable Batch Sizes

The inventors have found that these found equivalent relations are suitable for arbitrary batch sizes of luminol and permit the production of the desired form I in a reproducible manner.

Anhydrate Form II:

Production Example I for Crystalline Form II

The inventors have found a method for producing crystalline form II, wherein under aqueous conditions luminol is mixed with a sodium hydroxide solution, and by addition of 2-propanol, the solubility product of the luminol sodium salt is reduced such that the latter begins to precipitate. The precipitated luminol sodium salt is washed with 2-propanol and dried until constant masses are obtained.

Production Example I

Crystalline Form II—Embodiment II

In a preferred embodiment crystalline form II is produced using the following equivalents of reactants. A solution of 1.0-2.0 equivalents sodium hydroxide, preferably 1.1-1.4 equivalents sodium hydroxide, particularly preferably 1.2 equivalents sodium hydroxide, is produced in 6-7.5 vol/m water, to which 0.5-1 equivalent luminol is added. The reaction mixture is stirred until complete dissolution is achieved. Then, 2-propanol (60-120 vol/m) is added dropwise at room temperature (25° C.±5° C.) within approx. 10-40 min. The luminol sodium salt precipitates as a sediment. After complete addition, the reaction mixture is stirred at room temperature (25° C.±5° C.). The product is filtered, washed with a low-molecular alcohol, preferably 2-propanol (approx. 13-16 vol/m) and optionally dried in the vacuum compartment drier at 85° C.-120° C./1-3 mbar, preferably 90° C./1-3 mbar, or at the rotary evaporator at 85° C.-120° C./20±10 mbar.

Production Example I

Crystalline Form II—Embodiment III

In a particularly preferred embodiment, equivalents and batch sizes for producing crystalline form II are presented, and this applies for arbitrary batch sizes of luminol and is shown exemplarily in the following for a batch size of luminol of 10 g:

| Substance | Equivalents | Batch | Quantity [mol] |
|---|---|---|---|
| Luminol | 1 | 10 g | 56.5 |
| Sodium hydroxide | 1.2 | 2.7 g | 67.5 |
| Water for luminol solution | 6 (vol/m) | 60 mL | N/A |
| 2-Propanol abs. | 60 (vol/m) | 600 mL | N/A |
| 2-Propanol abs. for washing | 15 (vol/m) | 150 mL (3 × 50 mL) | N/A |

1.2 equivalents of sodium hydroxide and 1 equivalent of luminol is dissolved in water (6 vol/m). A clear solution is formed. This solution should be processed immediately, since it will get darker. Then, 2-propanol (60 vol/m) is added at room temperature (25° C.±5° C.) within approximately 20 min, and a sediment of luminol sodium salt is formed. The suspension is stirred at room temperature for 1-5 h, preferably 2 h, particularly preferably 3 h. The product is filtered, washed with 2-propanol (approx. 15 vol/m) and optionally dried in the vacuum compartment drier at 85° C.-120° C./1-3 mbar, preferably 90° C./1-3 mbar or at the rotary evaporator at 85° C.-120° C./20±10 mbar, preferably 90° C./20±10 mbar until constant masses are obtained.

Production Example I for Crystalline Form II

Embodiment IV

The inventors further demonstrate a method that is suitable for batch sizes of luminol of at least 300 g, preferably 400 g, particularly preferably 500 g, and that is described exemplarily for a batch size of 785 g:

| Substance | Equivalents | Batch | Quantity [mol] |
|---|---|---|---|
| Luminol | 1 | 785 g | 4.43 |
| Sodium hydroxide | 1.2 | 212 g | 5.32 |
| Water for luminol solution | 6 (vol/m) | 4,700 mL | N/A |
| 2-Propanol abs. | 60 (vol/m) | 47,000 mL | N/A |
| 2-Propanol abs. for washing | 13 (vol/m) | 10.5 l (3 × 3.5 l) | N/A |

A solution of 212 g (5.32 mol, 1.2 eq.) sodium hydroxide in 4,700 mL water is produced (80 l reactor). The luminol (785 g, 4.43 mol) is added to the sodium hydroxide solution and is stirred until dissolution thereof is achieved. A clear, brown solution results, to which the 2-propanol (60 vol/m) is added over a time of 20-30 min, preferably 30 min. The luminol sodium salt precipitates as a sediment. After complete addition, the mixture is restirred for at least 10 h, preferably 12 h, at room temperature (25° C.±5° C.) The mixture is filtered, the filter cake is washed with 2-propanol (13 vol/m) and optionally dried in the vacuum compartment drier at 85° C.-120° C./1-3 mbar, preferably 90° C./1-3 mbar or at the rotary evaporator at 85° C.-120° C./20±10 mbar, preferably 90° C./20±10 mbar until constant masses are obtained.

Production Example I

Crystalline Form II—Scalable Batch Sizes

The inventors have found that these found equivalent relations are suitable for arbitrary batch sizes of luminol and permit the production of the desired form II in a reproducible manner. When using higher quantities of luminol (500 g) and volumes, care should be taken that the stirring time is selected correspondingly long, in order to obtain a highest possible yield of end product.

Production Example II for Crystalline Form II (Recrystallization)

The inventors have found that crystalline form II can be produced by recrystallization of crystalline form I using the following equivalents: 2-propanol (10 vol/m) with a degree of purity of 70-90%, preferably 80-90%, particularly preferably 90%, is added to a solution of 1 equivalent form I and stirred for at least 10-14 h, preferably 10-12 h, at room temperature (25° C.±5° C.) The mixture is filtered, and the filter cake is washed with 2-propanol (approx. 20 vol/m) and optionally dried in the vacuum compartment drier at 85° C.-120° C./1-3 mbar, preferably 90° C./1-3 mbar, or at the rotary evaporator at 85° C.-120° C./20±10 mbar until constant masses are obtained.

Production Example II for Crystalline Form II

Recrystallization of Form I—Scalable Batch Sizes

A recrystallization method found by the inventors can be used with the following equivalents for arbitrary batch sizes, exemplarily described for a batch size of form I of 1 g:

| Substance | Equivalents | Batch | Quantity [mol] |
|---|---|---|---|
| Form II | 1 | 1 g | 5.02 |
| Water for solution 2-propanol | 1 (vol/m) | 1 mL | N/A |
| 2-Propanol | 9 (vol/m) | 9 mL | N/A |
| 2-Propanol for washing | approx. 20 (vol/m) | 20 mL (2 × 10 l) | N/A |

Crystalline form I (1 g) is suspended in aqueous 2-propanol (10-20% water) and stirred for at least 10 h, preferably 10-14 h, particularly preferably 10-12 h at room temperature (25° C.±5° C.) After filtration of the remaining solvents, the filter cake is washed with 2-propanol (2×10 mL) and dried at the rotary evaporator at 90° C./20 mbar until constant masses are achieved.

LIST OF ABBREVIATIONS

μg microgram
ALT alanine aminotransferase
approx. approximately
AST aspartate aminotransferase
CFU colony-forming units
DMSG German Multiple Sclerosis Association
e.g. for example
EMEA European Medicines Agency
g gram
GOT glutamate oxalacetate transaminase
GPT glutamate pyruvate transaminase
IL Interleukin
l liter
loc.cit. in the place cited
LPS lipopolysaccharide
mL milliliter
MW mean value
ng nanogram
pg picogram
SEM scanning electron microscope STD standard deviation
TNF tumor necrosis factor
U international units
vol/m volume unit per mass unit

The invention claimed is:

1. A crystalline polymorph form of a 5-amino-2,3-dihydrophthalazine-1,4-dione alkali salt, wherein said crystalline polymorph form is either form I or form II which are characterized by the following crystallography values determined by means of x-ray powder diagrams:
   form I:
      d values: 13.5; 6.9; 5.2; 4.6; 3.9; 3.5; 3.4; 3.3; 3.1; 3.0 and/or
      2-theta values: 6.5; 12.7; 16.9; 19.3; 22.8; 25.8; 26.6; 27.2; 28.7; 30.3 and
   form II:
      d values: 12.9; 7.9; 7.1; 6.5; 5.3; 4.0; 3.7; 3.6; 3.3; 3.2 and/or
      2-theta values: 6.8; 11.2; 12.5; 13.7; 16.7; 22.4; 24.3; 24.9; 27.2; 27.8.

2. The crystalline polymorph form according to claim 1, wherein said crystalline polymorph form has a content of water of crystallization ≤0.4%.

3. The crystalline polymorph form according to claim 1, wherein said form is form I.

4. The crystalline polymorph form according to claim 1, wherein said form is form II.

5. A pharmaceutical composition comprising a crystalline polymorph form according to claim 1 and at least one pharmaceutically suitable auxiliary substance.

6. The pharmaceutical composition according to claim 5, wherein said composition further contains one or more other active ingredients.

7. A method for producing the crystalline polymorph form according to claim 1, said method comprising:
   mixing 5-amino-2,3-dihydrophthalazine-1,4-dione with sodium hydroxide solution and adding a low-molecular liquid alcohol, thereby reducing the solubility product of the generated 5-amino-2,3-dihydrophthalazine-1,4-dione sodium salt such that the latter precipitates, and
   separating and drying the precipitated crystalline product, wherein crystalline form I can be suspended several times in ethanol, stirred, rewashed with ethanol and again dried.

8. The method according to claim 7, wherein said polymorph form is form I, and the added low-molecular alcohol is ethanol having a degree of purity ≥98%, and said ethanol is added at room temperature within 10-40 min.

9. The method according to claim 7, wherein said polymorph form is form II, and the added low-molecular alcohol is 2-propanol having a degree of purity ≥98%, and said 2-propanol is added at room temperature within 10-40 min.

10. A method for producing the crystalline polymorph form I according to claim 1, said method comprising:
   a) Producing a mixture of 1.0-1.4 equivalents sodium hydroxide, with 4-7 equivalents (vol/m) water;
   b) Adding 1 equivalent luminol to said mixture and stirring until complete dissolution is achieved;
   c) Adding 50-70 equivalents (vol/m) ethanol with a degree of purity ≥98%, at room temperature (25° C. ±5° C.) within 10-40 min;
   d) After complete addition of the ethanol, restirring the reaction mixture at room temperature for maximum 20 h, and filtering this mixture;
   e) Washing the resultant filter cake with 10-15 equivalents (vol/m) ethanol having a degree of purity ≥98%; and
   f) Drying the resultant product in a vacuum compartment drier at 50-90° C./1-3 mbar or in a rotary evaporator at 20±10 mbar and 50° C.-90° C., until constant masses are obtained.

11. A method for producing crystalline polymorph form II according to claim 1, said method comprising:
   a) Producing a mixture of 1.0-2.0 equivalents sodium hydroxide with 6-7.5 equivalents (vol/m) water;
   b) Adding 0.5-1 equivalent luminol and stirring the mixture until complete dissolution is achieved;
   c) Adding 60 equivalents (vol/m) 2-propanol with a degree of purity >98% within 20±10 min, at room temperature (25° C. ±5° C.);
   d) Stirring the resultant suspension at room temperature (25° C. ±5° C.) for at least 1 h;
   e) Filtering and washing the resultant filter cake with 13-15 equivalents (vol/m) 2-propanol with a degree of purity ≥98%; and
   f) Drying the resultant product in a vacuum compartment drier at 85° C.-120° C./1-3 mbar or in a rotary evaporator at 20±10 mbar and 85° C.-120° C., until constant masses are obtained.

12. The method according to claim 11, wherein in d) the stirring time is 1-5 h, or the stirring time is at least 10 h if the added luminol quantity is at least 200 g.

13. The method according to claim 8, wherein said ethanol has a degree of ≥99.

14. The method according to claim 9, wherein said 2-propanol has a degree of purity ≥99%.

15. The method for according to claim 10, wherein:
   said ethanol has a degree of purity ≥99%;
   after complete addition of the ethanol, the reaction mixture is restirred for 2-8 h;
   the filter cake is washed with ethanol having a degree of purity ≥99%; and
   the product is dried in a vacuum compartment drier at 70° C.-90° C./1-3 mbar, or in a rotary evaporator at 20±10 mbar and 50 70° C.-90° C.

16. The method for according to claim 11, wherein:
   said 2-propanol has a degree of purity ≥99%;
   the filter cake is washed with ethanol having a degree of purity >99%; and
   the product is dried in a vacuum compartment drier at 90° C.-100° C./1-3 mbar, or in a rotary evaporator at 20±10 mbar and 90° C.-100° C.

17. The method according to claim 12, wherein in d) the stirring time is 1-5 h, and the added luminol quantity is at least 300 g.

* * * * *